(12) United States Patent
Meier et al.

(10) Patent No.: US 9,011,920 B2
(45) Date of Patent: Apr. 21, 2015

(54) TRANSPORT-MEDIATING COLLOIDAL PHARMACEUTICAL COMPOUNDS

(75) Inventors: Bernd Horst Meier, Darmstadt (DE); Iris Theresia Jankowiak-Meier, Darmstadt (DE); Nele Meier, Darmstadt (DE); Clara Meier, Darmstadt (DE)

(73) Assignee: B. Braun Melsungen AG, Melsungen (DE)

( * ) Notice: Subject to any disclaimer, the term of this patent is extended or adjusted under 35 U.S.C. 154(b) by 278 days.

(21) Appl. No.: 13/131,903

(22) PCT Filed: Dec. 7, 2009

(86) PCT No.: PCT/EP2009/008718
§ 371 (c)(1),
(2), (4) Date: May 31, 2011

(87) PCT Pub. No.: WO2010/063491
PCT Pub. Date: Jun. 10, 2010

(65) Prior Publication Data
US 2011/0237657 A1   Sep. 29, 2011

(30) Foreign Application Priority Data

Dec. 6, 2008  (DE) .......... 10 2008 060 603
Mar. 31, 2009  (DE) .......... 10 2009 015 085
Jul. 8, 2009  (DE) .......... 10 2009 032 359

(51) Int. Cl.
*A61K 9/14* (2006.01)
*A61K 49/00* (2006.01)
*A61K 47/48* (2006.01)

(52) U.S. Cl.
CPC .......... *A61K 49/0054* (2013.01); *A61K 47/4823* (2013.01)

(58) Field of Classification Search
CPC .............................. A61K 47/36; A61K 47/38
USPC .......................................................... 424/488
See application file for complete search history.

(56) References Cited

U.S. PATENT DOCUMENTS

| | | | |
|---|---|---|---|
| 7,541,328 B2 | 6/2009 | Hemberger et al. |
| 7,816,516 B2 | 10/2010 | Sommermeyer et al. |
| 2009/0053284 A1 | 2/2009 | Langer et al. |
| 2010/0298529 A1 | 11/2010 | Meier |

FOREIGN PATENT DOCUMENTS

| | | |
|---|---|---|
| DE | 10105921 | 8/2002 |
| EP | 0 051 354 A2 | 5/1982 |
| EP | 1152013 A1 | 11/1998 |
| EP | 1 994 946 A1 | 11/2008 |

(Continued)

OTHER PUBLICATIONS

Abstract of Article—Lee et al., "Controlled dual release of basic fibroblast growth factor and indomethacin from heparin-conjugated polymeric micelle," *Int. J. Pharm.*, Jan. 4, 2008, vol. 346(1-2), pp. 57-63.

(Continued)

*Primary Examiner* — Benjamin Packard
(74) *Attorney, Agent, or Firm* — Dority & Manning, P.A.

(57) ABSTRACT

The invention relates to transport mediator-bonded colloids comprising pharmaceutical substances or fluorescence markers, to a method for the production thereof, and to a pharmaceutical preparation comprising said compounds.

30 Claims, 1 Drawing Sheet

(56) References Cited

FOREIGN PATENT DOCUMENTS

| WO | WO 9602260 A1 | 2/1996 |
| WO | WO 0172283 A1 | 12/2001 |
| WO | WO 03074087 A1 | 9/2003 |
| WO | WO 2004024761 A1 | 3/2004 |
| WO | WO 2007101698 A2 | 9/2007 |
| WO | WO 2007101698 A3 | 9/2007 |
| WO | WO 2009135888 A2 | 11/2009 |
| WO | WO 2009135888 A3 | 11/2009 |

OTHER PUBLICATIONS

Abstract of Article—Kose et al., "Low-molecular-weight heparin-conjugated liposomes with improved stability and hemocompatibility," *Drug Deliv.*, 1998, vol. 5(4), pp. 257-264.

Search Report for PCT/EP2009/008718 dated May 28, 2010, 3 pages.

Abstract of WO Patent—WO 02/080979 dated Oct. 17, 2002, 2 pages.

Abstract of WO Patent—WO 2007/122269 dated Nov. 1, 2007, 1 page.

Article—Alexei V. Demchenko, "General Aspects of the Glycosidic Bond Formation," Handbook of Chemical Glycosylation: Advances in Stereoselectivity and Therapeutic Relevance, 2008 WILEY-VCH Verlag GmbH & Co. KGaA, 27 pages.

Abstract of European Patent—EP1230935 dated Aug. 10, 2005, 2 pages.

Article—Köse et al., "Low-Molecular-Weight Heparin-Conjugated Liposomes with Improved Stability and Hemocompatibility," *Drug Delivery*, vol. 5, 1998, pp. 257-264.

Abstract of Article—Yang Shumin, "Use of Oligosaccharides as a New Feed Additive in Animal Feeding: A Review," *ACTA Zoonutrimental Sinica*, vol. 11, No. 1, Jan. 1999, pp. 1-9.

Machine Translation of WO 2007/122269, Nov. 1, 2007, 36 pages.

Article—Bajpai at al,, "Dynamics of controlled release of heparin from swellable corsslinked starch microspheres," *J. Mater Sci: Mater. Med.*, vol. 18, 2007, pp. 613-1621.

Fig.1

Fig.2

TRANSPORT-MEDIATING COLLOIDAL PHARMACEUTICAL COMPOUNDS

CROSS REFERENCE TO RELATED APPLICATION

This application is the national stage entry of International Patent Application No. PCT/EP2009/008718 having a filing date Dec. 7, 2009, which claims priority to and the benefit of German Patent Application No. 102008060603.0 filed in the German Intellectual Property Office on Dec. 6, 2008 , German Patent Application No. 102009015085.4 filed in the German Intellectual Property Office on Mar. 31, 2009 , and German Patent Application No. 102009032359.7 filed in the German Intellectual Property Office on Jul. 8, 2009 , the entire contents of which are incorporated herein by reference.

The invention relates to colloids bound to transport mediators that may comprise medicinal compounds or fluorescent markers, to a process for the preparation thereof, and to a pharmaceutical formulation containing such compounds.

The covalent binding to colloids enables substances to be introduced by phagocytosis into cells of the immune system, which would not be taken up, or if so only in negligible amounts, without such modification. EP 1 230 935 A1 describes the chemical binding of medicinally active substances to a polysaccharide to form a linker. The uptake of substances by correspondingly specialized cells of the reticulohistiocytic system has been demonstrated for a wide variety of colloids and particles. However, the introduction of larger molecules into cells of the body that are not specialized in phagocytosis is a problem. In addition, particles and colloids phagocytosed by macrophages are very quickly taken up into lysosomes after uptake into the cell, where they are degraded by a variety of lytic enzymes. The enzymatic potential of lysosomes is high; a wide variety of medicinal compounds is degraded correspondingly quickly by lysosomal enzymes. Of *Chlamydia trachomatis*, it is known that this bacterium is taken up by eukaryotic epithelial cells without being degraded enzymatically in the lysosomes. This uptake can be significantly reduced by the presence of heparins or heparin sulfate. Stephens et al. (Infection and Immunity, March 2000, p. 1080-1085, Vol. 68, No. 3) show that this effect is based on blocking of the heparin binding domain.

Conversely, the authors show that polystyrene microspheres are taken up into eukaryotic cells by endocytosis after being coated with heparin. Heparin itself binds to a wide variety of enzymes. Patients having an increased superoxide dismutase activity in the blood serum often exhibit a mutated variant of the enzyme (CHU et al. Arteriosclerosis, Thrombosis, and Vascular Biology. 2006; 26:1985).

The mutated variant (R213G) has a glycine instead of the amino acid arginine on position 213. Therefore, binding of the enzyme to heparin is not possible. Therefore, the afflicted patients have an increased activity for the enzyme, because the enzyme is mainly present in the serum rather than in the cell. For bearers of this genetic defect, this means a 2.3 times increased risk of the occurrence of ischemic heart diseases. EP 083 768 A1 describes direct heparin-protein conjugates in which the terminal aldose of heparin is bound to the N-terminal amino group of a serpin in order to enhance the effect of serpins on blood coagulation and respiratory distress syndromes. After being coupled to heparins, proteins and enzymes are very quickly cleared from the serum. Small proteins of below 70 kDa disappear almost completely already during the first kidney passage. In addition, a wide variety of proteins are known to present problems of stability and solubility, which can be favorably influenced by covalent binding to a water-soluble polysaccharide.

Heparin belongs to the group of glucosaminoglycans, which consist of linear chains of sulfated disaccharide units. Each disaccharide unit consists of one hexuronic acid each, which is variably composed of glucuronic or iduronic acid and 2-amino-2-deoxy-D-glucose or N-sulfo-D-glucosamine. Like polysaccharides, heparin and glucosaminoglucans have a free aldehyde group at the terminal end. Heparin occurs intracellularly almost exclusively in mast cells. However, more highly sulfated heparins, or heparin sulfates, are found almost everywhere on the cell membranes of higher mammals irrespective of the kind of organs.

The anticoagulant effect of heparin is primarily based on its affinity to the serin protease inhibitor antithrombin III. The smallest heparin unit that has such effect on AT III includes 5 saccharide units with a 3-O-sulfate group at the glucosamine group. This pentasaccharide can form a heparin/ATIII complex, which inhibits the coagulation factor Xa. Thrombin can also be inhibited by binding to specific heparin structures, but which are not present on a pentasaccharide, which only has 5 saccharide units. For the inhibition of thrombin, heparin compounds having at least 18 saccharide units are necessary.

The molecular size and degree of sulfatation are of critical importance not only in the selective effect of heparin on coagulation factors, but also in the interaction with a wide variety of endogenous cytokines and growth factors. The interaction of heparin with the fibroblast growth factor (FGF) requires a minimum number of 18 glucosaminoglucan units with a specific sulfatation of the oxygen atom present at C2. Sulfated heparins from 8 saccharide units exhibit an inhibitory effect on angiogenesis. For these sulfated octasaccharides, inhibition of angiogenesis in tumor cells is discussed. At the same time, these heparins seem to have no effect on blood coagulation. The molecular size and chemical properties, such as the number and localization of the sulfate, carboxy and amino groups, have a critical influence on the effect of heparins. The sulfate groups and, less importantly, the carboxy groups of the iduronic and glucuronic groups have the effect that heparin is one of the most strongly electronegatively charged molecules in mammals. The molecular size as well as the quantity and position of the sulfate and carboxy groups produce a specific charge pattern or a specific charge distribution on the heparin molecules. The specific charge distribution plays a critical role in the affinity of the compounds for procoagulant proteins and proteases, and also for the heparin binding domains of endothelial cells. The transport-mediating function of the heparins, which is displayed on cell membranes, is even more strongly dependent on the charge structure of the gluco-saminoglucan. Therefore, the covalent incorporation of heparins into water-soluble polysaccharides as transport mediators is essentially distinguished from the incorporation of the medicinally active compounds. If possible, the heparin should be coupled to the colloid in such a way that a binding site with a defined number of disaccharide units and charges stereoselectively matches the heparin binding domain of the cells. This means that this segment of the heparin remains chemically unbonded and, in addition, non-sterically hindered by the remaining molecule. As with the specific effect of heparin on ATIII and thrombin, the chain length and number of the sulfated hexuronic acid and aminodeoxyglucose units freely protruding from the polysaccharide are of great importance also in this case. In addition, there are indications that the segments of the heparin molecule relevant to the heparin binding domains are found rather in the middle of the heparin molecule. The part of the molecule utilized for the described association with the binding domains is strongly electronegatively charged due to the carboxy and sulfate groups. The blocking or disturbing of this stereospecifically relevant charge pattern by the covalent binding with the polysaccharide by means of a linker should be prevented for these sites if possible.

Being a strictly linear glucosaminoglucan, heparin has functional groups that can be utilized for binding to other molecules. In the region of iduronic and glucuronic acid, carboxy groups are present at C6. There are hydroxy groups at C2 and C3 and C1 of the first saccharide unit. Every second saccharide group bears an amino group at the C2 atom. This amino group and the carboxy group may be sulfated. Finally, heparin bears an aldehyde group at the terminal end.

It is known that point mutations in some genes coding for proteins result in a substitution of diaminomonocarboxylic acids by other amino acids. In some of these cases (superoxide dismutase), this change of the amino acid sequence is accompanied by a loss of the ability to bind to heparin sulfates, whereby the protein is no longer transported into the cell. These results also demonstrate that the incorporation of heparins into macromolecules as transport mediators, i.e., for the purpose of regulating the passage through cell membranes, is dependent on regioselective conditions on the part of the macromolecule. Here, a loss of amino groups not linked by peptide linkages means loss of the ability to incorporate the transport mediator heparin. In medical technology, it is frequently tried to prevent the formation of blood clots at implants by the non-specific covalent bonding to heparin.

For the introduction of medicinally active substances into specific organs and cell systems of the body, the following conditions must be met:
1. The uptake of the bound medicament is also effected in cells that are not specialized in phagocytosis.
2. After the passage through the outer cell membrane, the bound medicament shall not be taken up in lysosomes, and shall not be degraded enzymatically.
3. The medicament complex, which consists of the medicament chemically bonded to a transport mediator and/or a colloid, should be water-soluble and circulate in the blood for a sufficient period of time.
4. The medicament complex should have no influence on blood clotting.

Surprisingly, it has now been found that bonding of a transport mediator to a colloid (colloid-active compound) solves the above mentioned problems and serves, in particular, as a suitable transport system for medicaments and/or fluorescence markers covalently linked thereto. This holds, in particular, when the colloid and transport mediator are stereoselectively linked together. In addition, it has been surprisingly found that the bonding product can bind to membrane-bound and intracellular binding domains if the stereospecific structures of the transport mediator/colloid compound remain free for association and binding to the cellular binding domains.

The present invention relates to a compound of general formula (I)

wherein
T is a transport mediator;
P is a colloid-active compound;
Z is a first linker by means of which T and P are covalently linked together; and
n is an integer of at least 1;
and wherein the transport mediator T and/or the colloid P bears m groups -(L-A), wherein A is a medicinally active substance or a fluorescence marker;
L is a second linker through which P is covalently linked with A, or through which T is covalently linked with A; and
m is an integer that is 0 or at least 1.

Preferably, the transport mediator T has at least one binding site for association to cellular binding domains.

According to the invention, the transport mediators T are distinct from the colloids P.

Transport mediators T according to the present invention favor uptake into cells.

The transport mediator T is a glycan, more preferably selected from the group consisting of sialic acid, polysialic acid, neuraminic acid, N-acetylneuraminic acid, mannose, N-acetylmannose, N-propanolmannosamine, fucose, N-acetylfucose, galactose, N-acetylgalactose, glucose, N-acetylglucose, hexoses, N-acetylhexoses, ceramides, glucose-6-phosphate, mannose-6-phosphate, glucosylphosphatidylinositol, retinic acid, immunoglobulins, monoglycerates, diacylglycerates, sphingomyelin, bisphosphonates, glycoproteins, and glycosaminoglycans.

The glycosaminoglycans or glycosaminoglycan derivatives have proven to be particularly suitable transport mediators T.

Therefore, in a preferred embodiment, the transport mediator T is selected from the group consisting of heparin and heparin sulfate, especially heparin or heparin sulfate having less than 6 saccharide units. Heparins having less than 6 saccharide units as transport mediators have the particular advantage that the possibly occurring induction of autoantibodies can be substantially avoided with these heparins.

The colloid-active compound P (also simply referred to as "colloid P" in the following) is preferably selected from the group consisting of amyloses, amylopectins, acemannans, arabinogalactans, galactomannans, galactoglucomannans, xanthans, carrageenan, starch and modified starch.

The modified starches have proven particularly suitable. Starches can be modified, for example, by hydroxyalkylation or esterification. In addition, the starches may also be aminated, for example, by reductive amination.

Surprisingly, it has been found that amination of the colloid P by means of reductive amination can yield aminated colloids, especially modified starches, such as aminated hydroxyethyl starch or aminated carboxymethyl starch, which can be incorporated in the transport mediators with a high stereoselectivity in such a way that the compound obtained is very similar to the compounds taken up by body cells from transport mediator complexes.

In a preferred embodiment of the present invention, the linking of the transport mediator and colloid in effected stereoselectively. Further, it is preferred if the linking of the medicinally active substance or the fluorescence marker with the colloid and/or the transport mediator is also effected stereoselectively.

In a preferred embodiment, the colloid P is selected from the group consisting of hydroxyalkyl starches, esterified starches, carboxyalkyl starches, hydroxyalkyl carboxyalkyl starch, aminated hydroxyalkyl starch, aminated hydroxyalkyl carboxyalkyl starch and aminated carboxyalkyl starch.

Carboxyalkyl starches are preferably selected from carboxymethyl starch and carboxyethyl starch.

Advantageously, other specific units that allow the chemical bonding of the medicinally active substance or of the fluorescence marker or of the transport mediator, for example, biotin, amino acids or units bearing sulfide groups, such as cysteine, can also be incorporated into the colloids.

More preferably, according to the present invention, colloid P is a modified starch selected from the group consisting of hydroxyethyl starch or aminated hydroxyethyl starch, especially a hydroxyethyl starch that has been aminated by reductive amination.

The hydroxyalkyl groups in the hydroxyethyl starch (HES) have been introduced into the molecule for impeding the enzymatic degradation of the starch in the serum and for improving the water solubility. The degree of substitution, DS, is defined as the ratio of the total number of substituted monomer units to the total number of monomer units. In the following, a degree of substitution, DS, is stated when substituents are introduced.

In another embodiment of the present invention, the colloid-active compound has an average molecular weight of from 20,000 to 800,000 daltons, preferably from 25,000 to 500,000 daltons, especially from 30,000 to 200,000 daltons.

The degree of substitution, DS, of the modified starches, especially hydroxyethyl starch, is preferably from 0.2 to 0.8, especially from 0.3 to 0.6.

As medicaments A, all substances may be used that can be incorporated in the above mentioned colloids and/or transport mediators T through a linker L.

The compounds according to the invention may optionally be linked with medicinally active compounds or fluorescence markers. Preferably, the medicinally active compound is selected from the group consisting of antibiotics, chemotherapeutics, cytostatic agents, antigens, oligonucleotides, mediators, false metabolic substrates, analgetics and cytotoxic substances.

The fluorescence markers are preferably selected from the group consisting of fluorescein isothiocyanate (FITC), phycoerythrin, rhodamide and 2-amino-pyridine.

In addition to purely medicinally active substances, fluorescence markers, for example, fluorescein isothiocyanate, may also be therapeutically employed in connection with the transport mediator/colloid complex. Some tumors are known to express membrane-bound binding domains in larger numbers, for example, in order to gain access to the vascular system (FGF receptors). The marking of transport mediator/colloid complexes according to the invention specific for such binding domains with fluorescence markers, such as fluorescein isothiocyanate (A. N. De Belder, K. Granath: Preparation and Properties of fluorescein-labelled dextrans, Carbohydrate Research, 30 (1973) 375-378) enables the surgeon to optically identify organ fractions having a larger number of cells with such binding domains after injection of this compound (near infrared fluorescence imaging, NIRF).

In the compound according to formula (I), $(T-Z)_n$—P, the transport mediator T is covalently linked with the colloid P through a first linker group Z. In a preferred embodiment of the present invention, the linker Z is a functional group selected from carboxylic acid ester, carboxylic acid amides, urethane, ether and amine groups or comprises at least one such functional group. More preferably, the covalent chemical linkage of T to P through the linker Z is reversible, i.e., can be cleaved again without difficulty, for example, enzymatically.

The second linker L, through which the colloid P is covalently linked with the medicinally active substance or fluorescence marker, or through which the transport mediator is covalently linked with the medicinally active substance or fluorescence marker, also corresponds to the first linker Z in its function and design. For the linker L, it is particularly advantageous if it can be cleaved off again without difficulty, for example, enzymatically, which causes the medicinally active substance and/or the fluorescence marker to be released.

The formation of the linker Z or L can be performed by means of methods described in the prior art for the formation of carboxylic acid esters, carboxylic acid amides, urethanes, ethers and amines.

In a preferred embodiment, the compound according to the invention is obtainable by a reaction of at least one free
    isocyanate group (—NCO);
    carboxy group (—COOH);
    carboxylic acid halide group (—CO-A, with A=Cl, Br or I);
    alkylenecarboxy group (—$(CH_2)_q$—COOH, with q=1-10);
    ester group (—COOR with R=organic radical);
    epoxy group;
    or nucleophilic leaving group;
of the underlying colloid P with a free
    hydroxy group (—OH)
of the underlying transport mediator T to form the linker Z, wherein said colloid P and/or transport mediator T is linked with m units -(L-A).

In another embodiment of the present invention, the compound according to the invention is obtainable by a reaction of at least one free
    hydroxy group (—OH)
of the underlying colloid P with a free
    isocyanate group (—NCO);
    carboxy group (—COOH);
    carboxylic acid halide group (—CO-A, with A=Cl, Br or I);
    alkylenecarboxy group (—$(CH_2)_q$—COOH, with q=1-10);
    ester group (—COOR with R=organic radical);
    epoxy group;
    or nucleophilic leaving group;
of the underlying transport mediator T to form the linker Z, wherein said colloid P and/or transport mediator T is linked with m units -(L-A).

In another embodiment of the present invention, the compound according to the invention is obtainable by a reaction of at least one free
    amino group (—$NH_2$)
of the underlying colloid P with a free
    isocyanate group (—NCO);
    carboxy group (—COOH);
    carboxylic acid halide group (—CO-A, with A=Cl, Br or I);
    alkylenecarboxy group (—$(CH_2)_q$—COOH, with q=1-10);
    ester group (—COOR with R=organic radical);
    epoxy group;
    or nucleophilic leaving group;
of the underlying transport mediator T to form the linker Z, wherein said colloid P and/or transport mediator T is linked with m units -(L-A).

Further, in a preferred embodiment, the compound according to the invention is obtainable by a reaction of at least one free
    isocyanate group (—NCO);
    carboxy group (—COOH);
    carboxylic acid halide group (—CO-A, with A=Cl, Br or I);
    alkylenecarboxy group (—$(CH_2)_q$—COOH, with q=1-10);
    ester group (—COOR with R=organic radical);

epoxy group;
or nucleophilic leaving group;
of the underlying colloid P with a free
    amino group (—NH$_2$)
of the underlying transport mediator T to form the linker Z, wherein said colloid P and/or transport mediator T is linked with m units -(L-A).

More preferably, the compound according to the invention is obtainable by a reaction of at least one free
    hydroxy group (—OH); or
    amino group (—NH$_2$)
of the underlying colloid P with a free
    isocyanate group (—NCO);
    carboxy group (—COOH);
    carboxylic acid halide group (—CO-A, with A=Cl, Br or I);
    alkylenecarboxy group (—(CH$_2$)$_q$—COOH, with q=1-10);
    ester group (—COOR with R=organic radical);
    epoxy group;
    or nucleophilic leaving group;
of the underlying transport mediator T to form the linker Z, wherein said colloid P and/or transport mediator T is linked with m units -(L-A).

According to the present invention, nucleophilic leaving groups are preferably selected from the group of halides and tosylates.

Further, the compounds according to the invention can be obtainable by the reaction of a diamine of general formula II $$R^1(\text{—NH}_2)_2 \qquad (II)$$

wherein R$^1$ is selected from
    a single bond;
    linear or branched, saturated or unsaturated, aliphatic or alicyclic hydrocarbyl groups with 1 to 22 carbon atoms;
    aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or
    heteroaryl, heteroaryl-C$_1$-C$_4$-alkyl and heteroaryl-C$_2$-C$_6$-alkenyl groups with 3 to 8 carbon atoms in the heteroaryl group and one or two hetero-atom(s) selected from N, O and S, which may be substituted with C$_1$-C$_6$ alkyl and/or C$_2$-C$_6$ alkoxy groups;
with a free functional group of the underlying transport mediator T and at least one free functional group of the underlying colloid P, which are independently selected from
    isocyanate group (—NCO);
    carboxy group (—COOH);
    carboxylic acid halide group (—CO-A, with A=Cl, Br or I);
    alkylenecarboxy group (—(CH$_2$)$_q$—COOH, with q=1-10);
    ester group (—COOR with R=organic radical);
    epoxy group;
    or nucleophilic leaving group;
to form the linker Z, wherein said colloid P and/or transport mediator T is linked with m units -(L-A).

Suitable diamines include, for example, 1,2-diaminoethane, 1,2- or 1,3-diaminopropane, 1,2-, 1,3- or 1,4-diaminobutane, 1,5-diaminopentane, 2,2-dimethyl-1,3-diaminopropane, hexamethylenediamine, 1,7-diaminoheptane, 1,8-diaminooctane, trimethyl-1,6-diaminohexane, 1,9-diaminononane, 1,10-diaminodecane, 1,12-diaminododecane, 1,2-diaminocyclohexane, 1,4-diaminocyclohexane, 1,3-cyclohexanebis(methylamine), 1,2-phenylenediamine, 1,3-phenylenediamine, 1,4-phenylenediamine, 4,4'-Ethylenedianiline, 4,4'-methylenedianiline, 4,4'-diaminostilbene, 4,4'-thiodianiline, 4-aminophenyldisulfide, 2,6-diaminopyridine, 2,3-diaminopyridine, 3,4-diaminopyridine, 2,4-diaminopyrimidine, 4,5-diaminopyrimidine, 4,6-diaminopyrimidine.

In addition, in a further embodiment of the present invention, the compounds according to the invention can be obtained by a reaction of a dial of general formula III $$R^2(\text{—OH})_2 \qquad (III),$$

wherein R$^2$ is selected from
    linear or branched, saturated or unsaturated, aliphatic or alicyclic hydrocarbyl groups with 2 to 22 carbon atoms;
    aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or
    heteroaryl, heteroaryl-C$_1$-C$_4$-alkyl and heteroaryl-C$_2$-C$_6$-alkenyl groups with 3 to 8 carbon atoms in the heteroaryl group and one or two hetero-atom(s) selected from N, O and S, which may be substituted with C$_1$-C$_6$ alkyl and/or C$_2$-C$_6$ alkoxy groups;
with a free functional group of the underlying transport mediator T and at least one free functional group of the underlying colloid P, which are independently selected from
    isocyanate group (—NCO);
    carboxy group (—COOH);
    carboxylic acid halide group (—CO-A, with A=Cl, Br or I);
    alkylenecarboxy group (—(CH$_2$)$_q$—COOH, with q=1-10);
    ester group (—COOR with R=organic radical);
    epoxy group;
    or nucleophilic leaving group;
to form the linker Z, wherein said colloid P and/or transport mediator T is linked with m units -(L-A).

Suitable diols include, for example, ethylene glycol, propylene glycol, butylene glycol, and neopentylglycol, pentanediol-1,5,3-methylpentanediol-1,5, bisphenol A, 1,2- or 1,4-cyclohexanediol, caprolactonediol (reaction product of caprolactone and ethylene glycol), hydroxyalkylated bisphenols, trimethylolpropane, trimethylolethane, pentaerythritol, hexanediol-1,6, heptanediol-1,7, octanediol-1,8, butanediol-1,4, 2-methyloctanediol-1,8, nonanediol-1,9, decanediol-1,10, cyclohexanedimethylol, di-, tri- and tetraethylene glycol, di-, tri- and tetrapropylene glycol, polyethylene and polypropylene glycols with an average molecular weight of from 150 to 15,000.

In another embodiment of the present invention, the compounds according to the invention are obtainable by a reaction of a dicarboxylic acid of general formula IV $$R^3(\text{—COOH})_2 \qquad (IV)$$

wherein R$^3$ is selected from
    a single bond;
    linear or branched, saturated or unsaturated, aliphatic or alicyclic hydrocarbyl groups with 1 to 22 carbon atoms;
    aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or
    heteroaryl, heteroaryl-C$_1$-C$_4$-alkyl and heteroaryl-C$_2$-C$_6$-alkenyl groups with 3 to 8 carbon atoms in the heteroaryl group and one or two hetero-atom(s) selected from N, O and S, which may be substituted with C$_1$-C$_6$ alkyl and/or C$_2$-C$_6$ alkoxy groups;

with a free functional group of the underlying transport mediator T and at least one free functional group of the underlying colloid P, which are independently selected from
amino group (—NH$_2$); or
hydroxy group (—OH)
to form the linker Z, wherein said colloid P and/or transport mediator T is linked with m units -(L-A), Suitable dicarboxylic acids include, for example, oxalic acid, malonic acid, succinic acid, glutaric acid, adipic acid, pimelic acid, azelaic acid, sebacic acid, maleic acid, fumaric acid, sorbic acid, phthalic acid, terephthalic acid, isophthalic acid, or agaric acid.

In particular, the compounds according to the invention may also be obtainable by the reaction of a dicarboxylic acid halide of general formula V $$R^4(\text{—CO-A})_2 \quad (V)$$

wherein A=Cl, Br or I, and R$^4$ is selected from
a single bond;
linear or branched, saturated or unsaturated, aliphatic or alicyclic hydrocarbyl groups with 1 to 22 carbon atoms;
aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or
heteroaryl, heteroaryl-C$_1$-C$_4$-alkyl and heteroaryl-C$_2$-C$_6$-alkenyl groups with 3 to 8 carbon atoms in the heteroaryl group and one or two hetero-atom(s) selected from N, O and S, which may be substituted with C$_1$-C$_6$ alkyl and/or C$_2$-C$_6$ alkoxy groups;
with a free functional group of the underlying transport mediator T and at least one free functional group of the underlying colloid P, which are independently selected from
amino group (—NH$_2$); or
hydroxy group (—OH)
to form the linker Z, wherein said colloid P and/or transport mediator T is linked with m units -(L-A).

In addition, in a further preferred embodiment, the compounds according to the invention are obtainable by the reaction of a diester of general formula VI $$R^5(\text{—COOR'})_2 \quad (VI)$$

wherein R' is a C$_{1-10}$ alkyl group and R$^5$ is selected from
a single bond;
linear or branched, saturated or unsaturated, aliphatic or alicyclic hydrocarbyl groups with 1 to 22 carbon atoms;
aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or
heteroaryl, heteroaryl-C$_1$-C$_4$-alkyl and heteroaryl-C$_2$-C$_6$-alkenyl groups with 3 to 8 carbon atoms in the heteroaryl group and one or two hetero-atom(s) selected from N, O and S, which may be substituted with C$_1$-C$_6$ alkyl and/or C$_2$-C$_6$ alkoxy groups;
with respectively one free functional group of the underlying transport mediator T and at least one free functional group of the underlying colloid P, which are independently selected from
amino group (—NH$_2$); or
hydroxy group (—OH)
to form the linker Z, wherein said colloid P and/or transport mediator T is linked with m units -(L-A).

More preferably, the compounds according to the invention are obtainable by the reaction of a diisocyanate of general formula VII $$R^6(\text{—NCO})_2 \quad (VII)$$

wherein R$^6$ is selected from
linear or branched, saturated or unsaturated, aliphatic or alicyclic hydrocarbyl groups with 1 to 22 carbon atoms;
aryl, aryl-C$_1$-C$_4$-alkyl and aryl-C$_2$-C$_6$-alkenyl groups with 5 to 12 carbon atoms in the aryl group, which may optionally be substituted with C$_1$-C$_6$ alkyl and/or C$_2$-C$_6$ alkoxy groups; or
heteroaryl, heteroaryl-C$_1$-C$_4$-alkyl and heteroaryl-C$_2$-C$_6$-alkenyl groups with 3 to 8 carbon atoms in the heteroaryl group and one or two hetero-atom(s) selected from N, O and S, which may be substituted with C$_1$-C$_6$ alkyl and/or C$_2$-C$_6$ alkoxy groups;
with respectively one free functional group of the underlying transport mediator T and at least one free functional group of the underlying colloid P, which are independently selected from
amino group (—NH$_2$); or
hydroxy group (—OH)
to form the linker Z, wherein said colloid P and/or transport mediator T is linked with m units -(L-A).

Suitable diisocyanates include, for example, toluoylene diisocyanate, bitoluoylene diisocyanate, dianisidine diisocyanate, tetramethylene diisocyanate, hexamethylene diisocyanate, m-phenylene diisocyanate, m-xylylene diisocyanate, C$_1$-C$_6$ alkylbenzene diisocyanate, 1-chlorobenzene 2,4-diisocyanate, cyclohexylmethane diisocyanate, 3,3'-dimethoxydiphenylmethane 4,4'-diisocyanate, 1-nitrobenzene 2,4-diisocyanate, 1-alkoxybenzene 2,4-diisocyanate, ethylene diisocyanate, propylene diisocyanate, cyclohexylene 1,2-diisocyanate, 3,3'-dichloro-4,4'-biphenylene diisocyanate, diphenylene diisocyanate, 2-chlorotrimethylene diisocyanate, butylene 1,2-diisocyanate, ethylidene diisocyanate, diphenylmethane 4,4'-diisocyanate, diphenylethane diisocyanate, 1,5-naphthalene diisocyanate, cyclohexane diisocyanate and isophorone diisocyanate.

More preferably, the compound according to the invention is obtainable by the reaction of a diepoxide with respectively one free functional group of the underlying transport mediator T and at least one free functional group of the underlying colloid P, which are independently selected from
amino group (—NH$_2$); or
hydroxy group (—OH)
to form the linker Z, wherein said colloid P and/or transport mediator T is linked with m units -(L-A).

In particular, 1,2,3,4-diepoxybutane or 1,2,7,8-diepoxyoctane have proven to be suitable diepoxides.

Compounds in which the linking of the transport mediator T and colloid P is effected by reductive amination have proven particularly advantageous. Thus, more preferably, the compounds according to the invention are obtainable by reductive amination of a colloid P having free amino groups (—NH$_2$) with a transport mediator T having at least one aldehyde or keto group, and wherein the colloid P and/or transport mediator T is linked with m units -(L-A).

Herein, the colloid P having amino groups is preferably selected from the group consisting of aminated starch, aminated hydroxyalkyl starch, aminated hydroxyalkyl carboxyalkyl starch, and aminated carboxyalkyl starch. Particularly preferred is aminated hydroxyalkyl starch, which may itself be obtained, for example, by reductive amination.

More preferably, the colloids P linked by reductive amination with transport mediators T include transport mediators selected from the group of heparin or heparin derivatives.

In a particularly preferred embodiment of the present invention, the transport mediator T is heparin, and the colloid P is a hydroxyethyl starch, and the first linker Z is an —NH group.

As already set forth above, the second linker L is preferably a functional group selected from carboxylic acid ester, carboxylic acid amide, urethane, ether and amine groups or comprises at least one such functional group.

Further, several colloids P may also be linked through the linker molecules L and/or Z to form larger clusters. This reaction may compete with the binding of A and/or T to the colloid P. According to the invention, the ratio of these competing reactions can be influenced by suitably modifying the process employed. This can be done most simply by changing the ratio of reagents and substrates employed and by modifying the molecular weight of the colloid. Further, reaction conditions such as the temperature, pressure and catalysts also influence the ratio of the two reactions.

The colloid P may have one or more transport mediators T linked through the first linker Z. The number of transport mediators T linked with the colloid P is defined by the parameter n. In a preferred embodiment of the present invention, n is an integer of from 1 to 10,000, preferably from 2 to 1000, more preferably from 5 to 500, especially from 10 to 100.

In a further preferred embodiment of the present invention, the transport mediator T and/or the colloid P is covalently linked through the second linker L with A, i.e., the medicinally active substance or fluorescence marker. Therefore, in a preferred embodiment of the present invention, the parameter m is an integer of at least 1, preferably m is an integer of from 1 to 10,000, more preferably from 2 to 1000, even more preferably from 5 to 500, especially from 10 to 100.

The present invention further relates to a pharmaceutical formulation comprising the compound according to the invention.

The pharmaceutical formulation according to the invention is preferably an aqueous formulation and more preferably an injectable one. Preferably, the compound according to the invention is in a concentration of from 0.0001 to 50% by weight, especially from 0.01 to 10% by weight, for example, from 0.1 to 5.5% by weight, respectively based on the total composition.

The present invention further relates to a process for preparing the compound according to the invention by linking a transport mediator T with a colloid-active compound P to form a linker Z through which T and P are covalently linked with one another, and wherein the colloid P and/or the transport mediator T is linked with m units -(L-A). The meanings of T, P, Z, L and A are the same as defined above.

In a preferred embodiment of the process according to the invention, the linking of the transport mediator T and colloid P is effected by reductive amination.

Herein, it is preferred that, in a first step, the colloid P, which is selected from the group consisting of aminated starch, aminated hydroxyalkyl starch, aminated hydroxycarboxyalkyl starch, and aminated carboxyalkyl starch, is reacted with a transport mediator T selected from the group of heparins or heparin derivatives in the presence of a reducing agent.

Preferably, the reducing agent is selected from the group consisting of $LiAlH_4$, $LiBH_4$, $NaBH_4$ and $NaBCNH_3$.

In another preferred embodiment of the preparation process according to the invention, a reductive amination of a modified starch, preferably a hydroxyalkyl starch or a carboxymethyl starch, is first effected in a preliminary step. The reductive amination is advantageously effected with ammonia or ammonium hydroxide in the presence of a catalyst. This reaction is preferably effected in a hydrogen atmosphere under elevated pressure, for example, from 10 to 300 bar, preferably from 20 to 100 bar, and at temperatures within a range of from 50 to 300° C., preferably from 80 to 200° C. Raney nickel or cobalt/nickel catalysts are used as catalysts.

The thus obtainable aminated modified starch may subsequently be linked with a transport mediator, for example, a glucosaminoglucan, in another reductive amination reaction.

In another embodiment of the process of the present invention, the transport mediator T, preferably the glucosaminoglucan, especially the heparin or the heparin derivative, is applied to an electrically charged support in a first step. Subsequently, the further coupling reaction with the colloid P is performed, wherein the transport mediator T is left on the charged support. Applying the transport mediator to the charged support has proven advantageous, since the ionically charged regions of the transport mediator T, especially of the heparin or a heparin derivative, will orient themselves towards the charge carrier, and therefore such regions are hardly accessible for the coupling reaction with the colloid P. Thus, specific binding domains of the transport mediator can be selectively obtained with this process.

In a particular embodiment of the present invention, heparin or a heparin derivative is employed as the transport mediator, and hydroxyethyl starch or carboxymethyl starch is employed as the colloid.

Preferably, the part of the heparin molecule intended for association to the heparin binding domain is associated with a body, preferably a nanostructured body, more preferably a positively charged one, and kept free from the covalent bonding into the hydroxyethyl starch and/or carboxymethyl starch molecule. For example, for this purpose, a copper plate may be coated with an insulator and freed from the insulator layer at selected sites by using a laser. It is particularly advantageous if the charge structures of the heparin binding domains are detected by scanning electron microscopy, and corresponding charge patterns for the immobilization of the heparin molecules are fired into the insulator layer. Also, the scanning electron microscopy can be used for introducing suitable charge patterns into the insulator layer of the association body. Corresponding applications of laser technology are known to the skilled person. The application of the transport mediator to a charged surface may also be effected directly by application to other positively charged molecules. Particularly suitable for this purpose are strongly positively charged polymers that are present in the form of a film as a polycation under the reaction conditions of the syntheses according to the invention. In linkers reacting under alkaline reaction conditions, chitosan, for example, is present as a polycation, to which heparin is readily associated. It is to be noted that when the heparin is covalently bound to the colloid P, especially hydroxyethyl starch, a linkage is not to be formed between a functional group of the chitosan and the polysaccharide, but only between the hydroxyethyl starch and the heparin.

The invention will be further illustrated by the following Examples, but without being limited thereto.

EXAMPLES

Example 1a

Linking of Fluorescein Isothiocyanate Coupled Hydroxyethyl Starch (FITC-HES) with Heparin 200 mg of heparin[1)] is dissolved in 10 ml of PBS (phosphate-buffered saline), pH 7.5, and the solution is pipetted onto a plate positively charged with a Van de Graaff generator. The plate is kept charged for 1 week until the solution has dried as a film. Onto the film, 0.2 ml of 1,2,7,8-diepoxyoctane (from ALFA-AESAR GmbH & Co. KG, Germany) is pipetted and distributed by rotation. According to the method described by DeBelder and Granath[2], 80 mg of hydroxyethyl starch (HES) [average molecular weight: 50 kDa; DS=0.4] is covalently bound to fluorescein isothiocyanate units (FITC-HES). The FITC-HES is dissolved in 10 ml of a mixture of 3 ml of 1 N NaOH and 7 ml of acetone, and dropped onto the charged plate with shaking. The mixture is adjusted to a pH of 10 and shaken every 30 minutes in a darkened room. After 12 hours, the solution is withdrawn, dialyzed against distilled water and subsequently freeze-dried. The reagent is taken up in 10 ml of PBS, pH=7.5. In an electrophoresis, the linking product migrates significantly faster than a FITC-HES not linked to heparin.

[1] Heparin (also abbreviated as HEP): the sodium salt was employed (of porcine origin), pH=7, average $M_w$=12-15 kDa, manufacturer: Changzhou Qianhong Bio-Pharma Co., Ltd., Jiangsu, China.
[2] A. N. De Belder and Kirsti Granath; Carbohydrate Research, 30 (1973), 375-378.

Example 1 b

Effectiveness of the FITC-HES-heparin Compound According to Example 1a 100 mg of dry substance of the FITC-HES-heparin compound synthesized in Example 1a) is dissolved in 5 ml of an aqueous 0.9% NaCl solution, and the solution is injected i.p. into a Wistar rat. After 6 hours, the animal was sacrificed under anesthesia, and the organs were removed.

From the spleen, a piece of tissue sized 0.6×0.8 cm was taken and placed in formalin over night. After an ascending ethanol series and methyl benzoate series, sections having a thickness of 6-8 μm were prepared. The preparations were observed with a fluorescence microscope at a wavelength of 450-490 nm.

Figure 1:
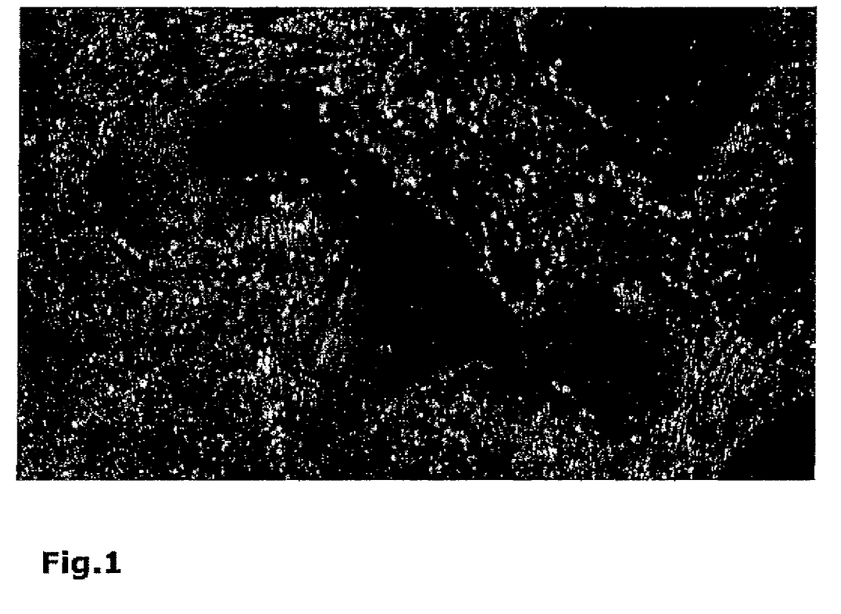
Figure 2:
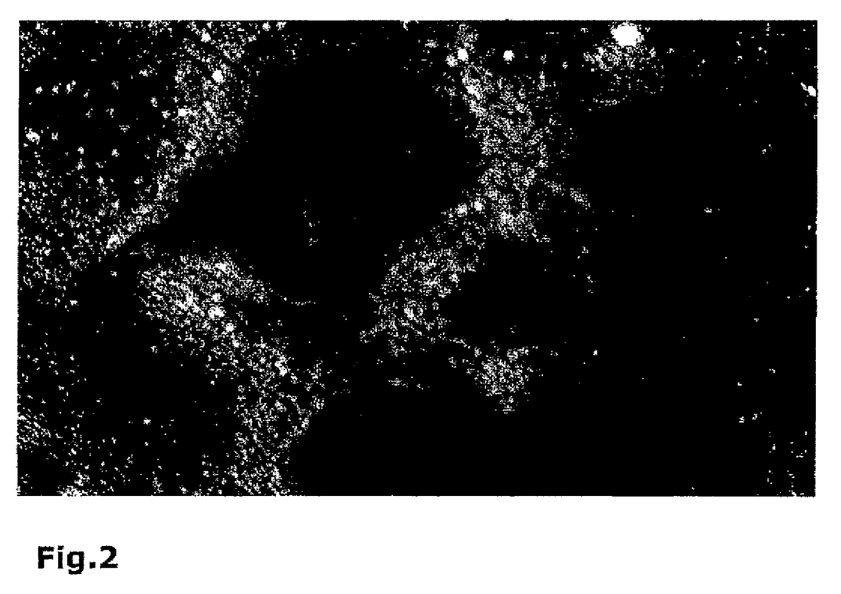

FIGS. 1 and 2 show a strong fluorescence of the cells at 20 times magnification. The bright areas in the photographs demonstrate the uptake of the fluorescence-marked HES-heparin complex into the tissue cells of the spleen.

Example 2

Linking of Carboxymethyl Hydroxyethyl Starch with Heparin 200 mg of heparin[1] is dissolved in distilled water and treated like in Example 1a). 10 ml of a 6% carboxymethyl hydroxyethyl starch [DS for carboxymethyl groups=0.06, and DS for the hydroxyethyl groups=0.34] is dissolved in 10 ml of a 0.1 N HCl acetone solution (3 ml of 0.1 N HCl and 7 ml of acetone) and added together with 0.2 ml 1,2,7,8-diepoxyoctane, followed by shaking.

The mixture is adjusted to a pH of 3 to 4 by adding the HCl/acetone solution and shaken every 30 minutes. After 12 hours, the solution is withdrawn, dialyzed against distilled water and subsequently freeze-dried.

Example 3

Linking of an Aminated HES with Heparin 200 g of a hydroxyethyl starch (HES) [average molecular weight Mw=50,000; DS=0.3] is placed into an autoclave together with a 27% ammonium hydroxide solution and 300 g of a nickel/copper/chromium catalyst with a nickel proportion of 75%, a copper proportion of 23% and a chromium proportion of 2%. Under addition of hydrogen, the autoclave is pressurized over a period of 12 hours. The temperature is adjusted to 220° C. Subsequently, the mixture is withdrawn, dialyzed and freeze-dried. 200 mg of heparin[1] is dissolved in 5 ml of PBS, pH=−7.5, and pipetted onto a Petri dish positively charged with a Van de Graaff generator. 200 mg of the reductively aminated hydroxyethyl starch is dissolved in 10 ml of distilled water, and the solution is carefully added. Thereafter, 0.025 mg of sodium cyanoborohydride $NaBH_3CN$ is admixed. The Petri dish is carefully shaken. After 2 hours, again 0.025 mg of the sodium cyanoborohydride is added, and the mixture is carefully shaken until bubbles cease to rise. The addition of sodium cyanoborohydride is repeated four times in the same way. Thereafter, the reagent is allowed to stand for 72 hours; finally, it is taken up in an excess of PBS, pH=7.5, dialyzed and freeze-dried.

Example 4

Linking of an Aminated HES with Heparin, Followed by Reaction with Human Albumin

200 g of a hydroxyethyl starch (HES) [average molecular weight Mw=50,000; DS=0.3] is placed into an autoclave together with a 27% ammonium hydroxide solution and 300 g of a nickel/copper/chromium catalyst with a nickel proportion of 75%, a copper proportion of 23% and a chromium proportion of 2%. Under addition of hydrogen, the autoclave is pressurized over a period of 12 hours. The temperature is adjusted to 270° C. Subsequently, the mixture is withdrawn, dialyzed and freeze-dried. 200 mg of heparin[1] is dissolved in 5 ml of PBS, pH=7.5, and pipetted onto a Petri dish positively charged with a Van de Graaff generator. 200 mg of the reductively aminated hydroxyethyl starch is dissolved in 10 ml of distilled water, and the solution is carefully added. Thereafter, 0.025 mg of sodium cyanoborohydride $NaBH_3CN$ is admixed. The Petri dish is carefully shaken. After 2 hours, again 0.025 mg of the sodium cyanoborohydride is added, and the mixture is carefully shaken until bubbles cease to rise. The addition of sodium cyanoborohydride is repeated four times in the same way.

Thereafter, the reagent is allowed to stand for 24 hours. After renewed charging by the Van de Graaff generator, 10 mg of human albumin in 10 ml of PBS (pH=7.5) is added. Subsequently, 0.025 mg of sodium cyanoborohydride $NaBH_3CN$ is added. The Petri dish is carefully shaken. The addition of 0.025 mg of sodium cyanoborohydride $NaBH_3CN$ followed by shaking is repeated four times with and four times without an operating Van de Graaff generator. The reagent is finally taken up in an excess of PBS (pH 7,5), dialyzed and freeze-dried.

Example 5

Linking of Hydroxyethyl Starch with Heparin Through hexane-1,6-diamine a) Tosylation of the Hydroxyethyl Starch

2305-BA-100

$HES_{40}$[3] (20 g) is suspended in pyridine (200 ml) and heated under reflux until a clear solution has formed. Thereafter, the solution is cooled down to 0° C., and tosyl chloride (19.4 g, 200 equ.) is added in portions with stirring, and the reaction solution is allowed to slowly warm up to room temperature. With stirring, the reaction solution is added to acetonitrile (500 ml). Immediately, a white precipitate forms, which is filtered off and dried under vacuum. The white foam obtained is co-evaporated with acetonitrile three times, the residue is taken up is distilled water, and dialyzed for 24 hours. After removing the water by evaporation, the title compound is obtained as a colorless solid (2.6 g). As compared to the pure $HES_{40}$, the $^1$H-NMR spectrum (400 MHz, $D_2O$) additionally shows typical symmetrical aromatic CH peaks with a chemical shift of 7-8 ppm, which indicate tosyl groups.

[3] $HES_{40}$: Hydroxyethyl starch having an average molecular weight $M_w$=40 kDa, degree of substitution DS=0.3; manufacturer: BBraun, Crissier, Switzerland.

b) Substitution of the Tosylated HES with Amino Linker

2305-BA-100

A solution of 2305-BA-100 (3.3 g) and hexanediamine (10.0 g, 1000 equ.) in DMF (5 ml) is stirred at 50° C. over night and then poured onto acetone (300 ml). The precipitated solid is filtered off and dried. For further purification, the raw product is dissolved in distilled water and dialyzed for 24 hours. After removing the water by evaporation, the above mentioned reaction product is obtained as a colorless solid (1.5 g). As compared to heparin, the $^1$H-NMR spectrum (400 MHz, $D_2O$) additionally shows typical $CH_2$ peaks with a chemical shift of 1-2 ppm, which indicate the amino linker.

c) EDC[4] Coupling of the Reaction Product Obtained in Step b) with HEP[1]

[4] EDC: N-dimethylaminopropyl-N-ethylcarbodiimide hydrochloride

To a solution of HEP (60 mg) and the product obtained in step b) (200 mg) in distilled water (4 ml), EDC[4] hydrochloride (80 mg, 100 equ.) is added. The reaction solution is stirred at room temperature over night and thereafter poured onto acetone (5 ml). The precipitated solid is filtered off and dried. For further purification, the raw product is dissolved in distilled water and dialyzed for 24 hours. After removing the water by evaporation, the linking product of HES and heparin as shown in the reaction scheme is obtained as a colorless solid (0.11 g).

Example 6

Linking of Hydroxyethyl Starch with Heparin Through hexane-1,6-diamine a) EDC[4] Coupling of Heparin (HEP) with Amino Linker To a solution of HEP (1.0 g) and hexane-1,6-diamine (0.8 g, 100 equ.) in distilled water (10 ml), EDC[4] hydrochloride (14 g, 100 equ.) is added. The reaction solution is stirred at 20° C. over night and then poured onto acetone (20 ml). The precipitated solid is filtered off and dried. By means of LC-MS, it is determined that unreacted hexanediamine is contained in the reaction product. For further purification, the raw product is dissolved in distilled water and dialyzed for 24 hours. After removing the water by evaporation, the coupling product shown in the reaction scheme is obtained as a colorless solid (0.8 g). As compared to heparin, the $^1$H-NMR spectrum (400 MHz, $D_2O$) additionally shows typical $CH_2$ peaks with a chemical shift of 1-2 ppm.

b) Nucleophilic Substitution of the Coupling Product Obtained in Step a) with the Tosylated HES from Example 5, Step a)

2305-AA-1

To a suspension of 2305-AA-1 (30 mg) and 2305-BA100 (100 mg, MW: about 50 kDa) in DMSO (4 ml), $Et_3N$ (0.003 ml, 100 equ.) is injected, followed by heating at 80° C. with stirring. The reaction mixture is stirred for 6 hours and thereafter poured onto acetone (6 ml). The precipitated solid is filtered off and dried. The title compound is obtained as a slightly beige solid (0.1 g). As compared to heparin, the $^1$H-NMR spectrum (400 MHz, $D_2O$) additionally shows typical $CH_2$ peaks with a chemical shift of 1-2 ppm.

Example 7

Linking of an Aminated Hydroxyethyl Starch with Heparin by Reductive Amination a) Amination of the Hydroxyethyl Starch (HES)

HES$_{40}$ (5.1 g, MW: 40 kDa) is dissolved in an aqueous ammonium hydroxide solution (100 ml, 22%). The catalyst consisting of nickel (5.6 g, 325 mesh), chromium (0.15 g, 100 mesh) and copper (1.8 g, 1 μm) is added to the solution. The mixture is stirred under a hydrogen atmosphere at 120° C. in an autoclave for 48 hours. After cooling to 20° C., the catalyst is filtered off, and the filtrate is poured onto ethanol (20 ml). The precipitated solid is filtered off, washed with little ethanol/water, and dried. The aminated HES is obtained as a slightly bluish solid (1.2 g).

b) Reductive Amination of the Aminated HES Obtained in Step a) with Heparin

HEP (200 mg) is dissolved in an aqueous phosphate buffer solution (5 ml, pH=7.5), and a solution of the aminated hydroxyethyl starch from step a) (200 mg) in distilled water (10 ml) is added dropwise. At intervals of 2 hours, NaCNBH$_3$ is added six times (0.025 mg each, from an aqueous stock solution) to the reaction solution. The reaction mixture is again stirred at 20° C. for 2 hours. For further purification, the raw product is dialyzed for 24 hours. After removing the water by evaporation, the linking product of heparin and aminated hydroxyethyl starch as shown in the reaction scheme is obtained as a colorless solid (250 mg).

Example 8

Linking of a Fluorescence-marked Heparin with an Aminated Hydroxyethyl Starch (HES) by Reductive Amination a) Coupling of Heparin (HEP) with the Fluorescence Marker 2-aminopyridine (HEP* = flourescence-marked)

To a solution of 2-aminopyridine (31.7 g, 0.33 mol, 1000 equ.) and NaCNBH$_3$ (2.1 g, 0.033 mol, 100 equ.) in formamide (50 ml), heparin (5.0 g) is added. The suspension obtained is stirred at 37° C. over night, and a clear solution is slowly formed. The reaction solution is poured onto EtOH (50 ml). The precipitated solid is filtered off and dried. The coupling product (HEP*) shown in the reaction scheme is obtained as a slightly beige solid (1.3 g). Both in aqueous solution and as a solid, the coupling product shows an intensive blue-purple fluorescence when irradiated with UV light at 366 nm. As compared to heparin, the $^1$H-NMR spectrum (400 MHz, D$_2$O) additionally shows typical aromatic CH peaks with a chemical shift of 6.6-7.8 ppm, which indicate typical pyridine substituents.

b) Linking of the Fluorescence-marked Heparin (HEP*) Prepared in Step a) with the Aminated Hydroxyethyl Starch Prepared in Example 7, Step a), by Reductive Amination HEP* from step a) (200 mg, average molecular weight: 15 kDa) is dissolved in an aqueous phosphate buffer solution (5 ml, pH=7.5), and a solution of the aminated HES from Example 7, step a) (200 mg), in distilled water (10 ml) is added dropwise. At intervals of 2 hours, NaCNBH$_3$ is added three times (0.025 mg each, from an aqueous stock solution) to the reaction solution. The reaction mixture is again stirred at 20° C. for 2 hours. For further purification, the raw product is dialyzed for 24 hours. After removing the water by evaporation, the linking product of aminated HES and fluorescence-marked heparin is obtained as a colorless solid (200 mg).

Both in aqueous solution and as a solid, the compound shows an intensive green-yellow fluorescence when irradiated with UV light at 366 nm. As compared to heparin, the $^1$H-NMR spectrum (400 MHz, D$_2$O) additionally shows typical aromatic CH peaks with a chemical shift of 7.0-7.8 ppm, which indicate typical pyridine substituents.

Example 9

Linking of the Product Obtained in Example 5, Step b), with the Fluorescence-marked Heparin from Example 8, Step a) by Coupling using EDC[4)]

To a solution of HEP* (Example 8, step a)) (60 mg) and the reaction product from Example 5, step b) (160 mg), in distilled water (4 ml), EDC hydrochloride (80 mg, 100 equ.) is added. The reaction solution is stirred at 20° C. over night and thereafter poured onto acetone (5 ml). The precipitated solid is filtered off and dried. For further purification, the raw product is dissolved in distilled water and dialyzed for 24 hours. After removing the water by evaporation, the desired linking product according to the formula scheme shown above is obtained as a colorless solid (0.1 g).

Both in aqueous solution and as a solid, the compound shows an intensive green-yellow fluorescence when irradiated with UV light at 366 nm. As compared to heparin, the $^1$H-NMR spectrum (400 MHz, D$_2$O) additionally shows typical aromatic CH peaks with a chemical shift of 7.0-7.8 ppm, which indicate typical pyridine substituents.

1) Heparin (also abbreviated as HEP): the sodium salt was employed (of porcine origin), pH =7, average M$_w$ =12-15 kDa, manufacturer: Changzhou Qianhong Bio-Pharma Co., Ltd., Jiangsu, China.

2) A. N. De Belder and Kirsti Granath; Carbohydrate Research, 30 (1973), 375-378.
3) HES$_{40}$: Hydroxyethyl starch having an average molecular weight M$_{w}$=40 kDa, degree of substitution DS=0.3; manufacturer: BBraun, Crissier, Switzerland.
4) EDC: N-dimethylaminopropyl-N-ethylcarbodiimide hydrochloride

The invention claimed is:

1. A compound of general formula (I)

(T-Z)$_n$—P  (I), wherein

T is a transport mediator in the form of heparin or a heparin derivative;

P is a colloid-active compound selected from the group consisting of hydroxyalkyl starches and carboxyalkyl starches;

Z is a first linker by means of which T and P are covalently linked together; and n is an integer of at least 1;

and wherein the transport mediator T and/or the colloid P is linked with m groups -(L-A), wherein A is a medicinally active substance, characterized in that said medicinally active substance A is selected from the group consisting of antibiotics, chemotherapeutics, cytostatic agents, antigens, oligonucleotides, mediators, false metabolic substrates, analgetics and cytotoxic substances;

L is a second linker through which P is covalently linked with A, or through which T is covalently linked with A; and m is an integer that is at least 1.

2. The compound according to claim 1, characterized in that said transport mediator has at least one binding site for association to cellular binding domains.

3. The compound according to claim 1, characterized in that said transport mediator T is selected from the group consisting of heparin and heparin sulfate.

4. The compound according to claim 1, characterized in that said colloid-active compound P is selected from the group consisting of hydroxyalkyl carboxyalkyl starch, aminated hydroxyalkyl starch, aminated hydroxyalkyl carboxyalkyl starch and aminated carboxyalkyl starch.

5. The compound according to claim 4, characterized in that said colloid-active compound P is selected from hydroxyethyl starch or aminated hydroxyethyl starch.

6. The compound according to claim 3, characterized in that said colloid-active compound has an average molecular weight of from 20,000 to 800,000 daltons, preferably from 25,000 to 500,000 daltons, especially from 30,000 to 200,000 daltons.

7. The compound according to claim 1, characterized in that the degree of substitution, hydroxyethyl starch is from 0.2 to 0.8.

8. The compound according to claim 1, characterized in that said linker Z is a functional group selected from carboxylic acid ester, carboxylic acid amides, urethane, ether and amine groups, or comprises such a group.

9. The compound according to claim 1, obtainable by a reaction of at least one free
   isocyanate group (—NCO);
   carboxy group (—COOH);
   carboxylic acid halide group (—CO-A, with A =Cl, Br or I);
   alkylenecarboxy group (—(CH$_2$)$_q$—COOH, with q = 1-10);
   ester group (—COOR with R =organic radical);
   epoxy group;
   or nucieophilic leaving group;
   of the underlying colloid P with a free
   hydroxy group (—OH)
   of the underlying transport mediator T to form the linker Z, wherein said colloid P and/or transport mediator T is linked with m units (L-A).

10. The compound according to claim 1, obtainable by a reaction of at least one free
    hydroxy group (—OH)
    of the underlying colloid P with a free
    isocyanate group (—NCO);
    carboxy group (—COOH);
    carboxylic acid halide group (—CO-A, with A =Cl, Br or I);
    alkylenecarboxy group (—(CH$_2$)$_q$—COOH, with q = 1-10);
    ester group (—COOR with R =organic radical);
    epoxy group;
    or nucleophilic leaving group;
    of the underlying transport mediator T to form the linker Z, wherein said colloid P and/or transport mediator T is linked with m units -(L-A).

11. The compound according to claim 1, obtainable by a reaction of at least one free
    amino group (—NH$_2$)
    of the underlying colloid P with a free
    isocyanate group (—NCO);
    carboxy group (—COOH),
    carboxylic acid halide group (—CO-A, with A =Cl, Br or I);
    alkylenecarboxy group (—(CH$_2$)$_q$—COOH, with q = 1-10);
    ester group (—COOR with R =organic radical);
    epoxy group;
    or nucleophilic leaving group;
    of the underlying transport mediator T to form the linker Z, wherein said colloid P and/or transport mediator T is linked with m units -(L-A).

12. The compound according to claim 1, obtainable by a reaction of at least one free
    isocyanate group (—NCO);
    carboxy group (—COOH);
    carboxylic acid halide group (—CO-A, with A =Cl, Br or I);
    alkylenecarboxy group (—(CH$_2$)$_q$—COOH, with q = 1-10);
    ester group (—COOR with R =organic radical);
    epoxy group;
    or nucleophilic leaving group;
    of the underlying colloid P with a free
    amino group (—NH$_2$)
    of the underlying transport mediator T to form the linker Z, wherein said colloid P and/or transport mediator T is linked with m units -(L-A).

13. The compound according to claim 1, obtainable by a reaction of at least one free
    hydroxy group (—OH); or
    amino group (—NH$_2$)
    of the underlying colloid P with a free
    isocyanate group (—NCO);
    carboxy group (—COOH);
    carboxylic acid halide group (—CO-A, with A =Cl, Br or I);
    alkylenecarboxy group (—(CH$_2$)$_q$—COOH, with q = 1-10);
    ester group (—COOR with R =organic radical);

epoxy group;
or nucleophilic leaving group;
of the underlying transport mediator T to form the linker Z, wherein said colloid P and/or transport mediator T is linked with m units -(L-A).

14. The compound according to claim 1, obtainable by a reaction of a diamine of general formula II $$R^1(-NH_2)_2 \qquad (II)$$

wherein $R^1$ is selected from
a single bond;
linear or branched, saturated or unsaturated; aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or
heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying transport mediator T and at least one free functional group of the underlying colloid P, which are independently selected from
isocyanate group (—NCO);
carboxy group (—COOH);
carboxylic acid halide group (—CO-A, with A =Cl, Br or I);
alkylenecarboxy group (—$(CH_2)_q$—COOH, with q = 1-10);
ester group (—COOR with R =organic radical);
epoxy group;
or nucleophilic leaving group;
to form the linker Z, wherein said colloid P and/or transport mediator T is linked with m units -(L-A).

15. The compound according to claim 1, obtainable by a reaction of a diol of general formula III $$R^2(-OH)_2 \qquad (III),$$

wherein $R^2$ is selected from
linear or branched, saturated or unsaturated, aliphatic or alicyclic hydrocarbyl groups with 2 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or
heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying transport mediator T and at least one free functional group of the underlying colloid P, which are independently selected from
isocyanate group (—NCO);
carboxy group (—COOH);
carboxylic acid halide group (—CO-A, with A =Cl, Br or I);
alkylenecarboxy group (—$(CH_2)_q$—COOH, with q = 1-10);
ester group (—COOR with R =organic radical);
epoxy group;
or nucleophilic leaving group;

to form the linker Z, wherein said colloid P and/or transport mediator T is linked with m units -(L-A).

16. The compound according to claim 1, obtainable by a reaction of a dicarboxylic acid of general formula IV $$R^3(-COOH)_2 \qquad (IV)$$

wherein $R^3$ is selected from
a single bond;
linear or branched, saturated or unsaturated, aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$alkyl and/or $C_2$-$C_6$ alkoxy groups; or
heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying transport mediator T and at least one free functional group of the underlying colloid P, which are independently selected from
amino group (—$NH_2$); or
hydroxy group (—OH)
to form the linker Z, wherein said colloid P and/or transport mediator T is linked with m units -(L-A).

17. The compound according to claim 1, obtainable by a reaction of a dicarboxylic acid halide of general formula V $$R^4(-CO-A)_2 \qquad (V)$$

wherein A =Cl, Br or I, and $R^4$ is selected from
a single bond;
linear or branched, saturated or unsaturated, aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$alkyl and/or $C_2$-$C_6$ alkoxy groups; or
heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;
with a free functional group of the underlying transport mediator T and at least one free functional group of the underlying colloid P, which are independently selected from
amino group (—$NH_2$); or
hydroxy group (—OH)
to form the linker Z, wherein said colloid P and/or transport mediator T is linked with m units -(L-A).

18. The compound according to claim 1, obtainable by a reaction of a diester of general formula VI $$R^5(-COOR')_2 \qquad (VI)$$

wherein R' is a $C_{1-10}$ alkyl group and $R^5$ is selected from
a single bond;
linear or branched, saturated or unsaturated, aliphatic or alicyclic hydrocarbyl groups with 1 to 22 carbon atoms;
aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with respectively one free functional group of the underlying transport mediator T and at least one free functional group of the underlying colloid P, which are independently selected from amino group (—$NH_2$); or hydroxy group (—OH)

to form the linker Z, wherein said colloid P and/or transport mediator T is linked with m units -(L-A).

19. The compound according to claim 1, obtainable by a reaction of a diisocyanate of general formula VII $$R^6(\text{—NCO})_2 \qquad (\text{VII})$$

wherein $R^6$ is selected from linear or branched, saturated or unsaturated, aliphatic or alicyclic hydrocarbyl groups with 1 to 22 carbon atoms;

aryl, aryl-$C_1$-$C_4$-alkyl and aryl-$C_2$-$C_6$-alkenyl groups with 5 to 12 carbon atoms in the aryl group, which may optionally be substituted with $C_1$-$C_6$ alkyl and/or $C_2$-$C_6$ alkoxy groups; or heteroaryl, heteroaryl-$C_1$-$C_4$-alkyl and heteroaryl-$C_2$-$C_6$-alkenyl groups with 3 to 8 carbon atoms in the heteroaryl group and one or two heteroatom(s) selected from N, O and S, which may be substituted with $C_1$-$C_6$ alkyl and/or $C_2$-$C_6$ alkoxy groups;

with respectively one free functional group of the underlying transport mediator T and at least one free functional group of the underlying colloid P, which are independently selected from amino group (—$NH_2$); or hydroxy group (—OH)

to form the linker Z, wherein said colloid P and/or transport mediator T is linked with m units -(L-A).

20. The compound according to claim 1, obtainable by a reaction of a diepoxide with respectively one free functional group of the underlying transport mediator T and at least one free functional group of the underlying colloid P, which are independently selected from amino group (—NH); or hydroxy group (—OH)

to form the linker Z, wherein said colloid P and/or transport mediator T is linked with m units -(L-A).

21. The compound according to claim 1, obtainable by reductive amination of a colloid P having free amino groups (—$NH_2$) with a transport mediator T having at least one aldehyde or keto group, and wherein the colloid P and/or transport mediator T is linked with m units -(L-A).

22. The compound according to claim 21, characterized in that said colloid P having amino groups is selected from the group consisting of aminated starch, aminated hydroxyalkyl starch, aminated hydroxyalkyl carboxyalkyl starch, and aminated carboxyalkyl starch.

23. The compound according to claim 1, characterized in that said transport mediator T is heparin, and said colloid P is a hydroxyethyl starch, and the first linker Z is an —NH group.

24. The compound according to claim 1, characterized in that said second linker L is a functional group selected from carboxylic acid ester, carboxylic acid amide, urethane, ether and amine groups, or comprises such a group.

25. A pharmaceutical formulation comprising the compound according to claim 1.

26. The pharmaceutical formulation according to claim 25, characterized in that said formulation is aqueous and injectable.

27. A process for preparing a compound of general formula (I) according to claim 1 by linking a transport mediator T with a colloid-active compound P to form a linker Z through which T and P are covalently linked with one another, and wherein the colloid P and/or the transport mediator T is linked with m units -(L-A).

28. The process according to claim 27, characterized in that the linking of the transport mediator T and colloid P is effected by reductive amination.

29. The process according to claim 27, characterized in that, in a first step, the colloid P, which is selected from the group consisting of aminated starch, aminated hydroxyalkyl starch, aminated hydroxycarboxyalkyl starch, and aminated carboxyalkyl starch, is reacted with a transport mediator T selected from the group of heparins or heparin derivatives in the presence of a reducing agent.

30. The process according to claim 29, characterized in that the reducing agent is selected from the group consisting of $LiAlH_4$, $LiBH_4$, $NaBH_4$ and $NaBH_3CN$.

* * * * *

UNITED STATES PATENT AND TRADEMARK OFFICE
CERTIFICATE OF CORRECTION

PATENT NO.       : 9,011,920 B2
APPLICATION NO.  : 13/131903
DATED            : April 21, 2015
INVENTOR(S)      : Bernd Horst Meier et al.

It is certified that error appears in the above-identified patent and that said Letters Patent is hereby corrected as shown below:

In the Claims

Claim 9 (column 20, line 2)

"...or nucieophilic leaving group;..." should read --...or nucleophilic leaving group;...--

Claim 9 (column 20, line 7)

"...linked with m groups (L–A)." should read --.. linked with m groups –(L–A).--

Claim 20 (column 23, line 44)

"...amino group (–NH); or..." should read --amino group (–NH$_2$); or...--

Signed and Sealed this
Fifteenth Day of September, 2015

Michelle K. Lee
*Director of the United States Patent and Trademark Office*